(12) United States Patent
Gauer (10) Patent No.: US 7,459,304 B2
(45) Date of Patent: Dec. 2, 2008

(54) METHOD FOR ANALYSING MACROMOLECULES

(75) Inventor: Christoph Gauer, München (DE)

(73) Assignee: Advalytix AG, Brunnthal (DE)

( * ) Notice: Subject to any disclaimer, the term of this patent is extended or adjusted under 35 U.S.C. 154(b) by 606 days.

(21) Appl. No.: 10/470,787

(22) PCT Filed: Dec. 19, 2001

(86) PCT No.: PCT/EP01/15032

§ 371 (c)(1),
(2), (4) Date: Dec. 30, 2003

(87) PCT Pub. No.: WO02/064821

PCT Pub. Date: Aug. 22, 2002

(65) Prior Publication Data

US 2004/0101975 A1    May 27, 2004

(30) Foreign Application Priority Data

Jan. 30, 2001    (DE)    ................. 101 03 954

(51) Int. Cl.
| | |
|---|---|
| C12M 1/34 | (2006.01) |
| C12Q 1/68 | (2006.01) |
| G01N 33/53 | (2006.01) |
| C07C 1/00 | (2006.01) |
| C07H 21/02 | (2006.01) |
| C07K 1/00 | (2006.01) |

(52) U.S. Cl. ................. 435/287.2; 435/6; 435/7.1; 204/157.15; 536/23.1; 530/350

(58) Field of Classification Search ............. 435/6, 435/7.1, 91.1, 287.1, 287.2; 436/94; 536/23.1, 536/24.3, 24.33; 530/300, 350; 204/155, 204/157.15
See application file for complete search history.

(56) References Cited

U.S. PATENT DOCUMENTS 5,474,796 A * 12/1995 Brennan ................. 427/2.13

(Continued)

FOREIGN PATENT DOCUMENTS

DE    19827900    4/1999

(Continued)

OTHER PUBLICATIONS

Attached definition for "surface wave" (printed on Jul. 21, 2008).*

(Continued)

*Primary Examiner*—Frank W Lu
(74) *Attorney, Agent, or Firm*—Dilworth & Barrese LLP (57) ABSTRACT

The invention relates to a method for the analysis of macromolecules using a microarray on which a plurality of first at least partly different macromolecules are located in a known arrangement, wherein the microarray is arranged on a solid surface on which a region is defined whose wetting properties differ from the surrounding solid surface such that a liquid with a plurality of second macromolecules preferably stays thereon, the liquid with the second macromolecules is brought onto the solid surface and at least partly removed and the second macromolecules remaining after the removal process are detected in order to determine from the position which of the first macromolecules have formed a bond with second macromolecules. The invention further relates to a method wherein a surface wave is launched to the liquid to distribute and/or thoroughly mix the liquid on the microarray.

8 Claims, 4 Drawing Sheets

U.S. PATENT DOCUMENTS

| | | |
|---|---|---|
| 5,653,939 A | 8/1997 | Hollis et al. |
| 5,674,742 A | 10/1997 | Northrup et al. |
| 5,874,219 A | 2/1999 | Rava et al. |
| 6,010,316 A | 1/2000 | Haller et al. |
| 6,589,726 B1 * | 7/2003 | Butler et al. .................... 435/6 |

FOREIGN PATENT DOCUMENTS

| | | |
|---|---|---|
| DE | 19940752 | 4/2000 |
| EP | 1053784 | 11/2000 |
| JP | 10-327590 | 12/1998 |
| WO | WO 94/05414 | 3/1994 |
| WO | WO 94/27719 | 12/1994 |
| WO | WO 99/43688 | 9/1999 |
| WO | WO 00/10011 | 2/2000 |
| WO | WO 00/16082 | 3/2000 |

OTHER PUBLICATIONS

Wang, Joseph, "From DNA Biosensors to Gene Chips," Nucleic Acids Research 2000, vol. 28, Nr. 16, 15, Aug. 2000, pp. 3011-3016.

* cited by examiner

METHOD FOR ANALYSING MACROMOLECULES

BACKGROUND OF THE INVENTION

The method relates to a method for the analysis of macromolecules using a microarray.

Such a method for the rapid analysis of macromolecules comprises the application in a regular arrangement on a so-called microarray. The densities which can presently be achieved on such a microarray are, for example, for DNA (deoxyribonucleic acid) up to 250,000 different species of molecules per $cm^2$. A parallel and rapid deposition of molecules can be achieved, for example, using so-called pipetting robots. An analysis, e.g. a fluorescence measurement, can easily be made in such an array geometry ("DNA Microarray", published by M. Schena, Oxford University Press, New York, 1999). Substances studied are, for example, antibodies, antigens, proteins or DNA.

In such a microarray different species of macromolecules are arranged at different locations in a matrix form. A liquid with another species of macromolecules is washed over the microarray and forms a specific bond with at least one species of macromolecules on the microarray. If the liquid is removed from the surface again, the macromolecules to be studied are only retained at the locations of the specific binding. With the aid of a spatially resolved measurement, e.g. a fluorescence measurement, it is possible to determine the locations at which the macromolecule to be studied is present. From the known position of the individual macromolecules in the matrix form of the microarray it is also possible to determine the species of macromolecules with which the macromolecule to be studied has formed a specific bond.

In this case, it must be ensured that the macromolecules to be studied can come in contact with all macromolecules in the matrix form. For this purpose, for example, the entire surface on which the microarray is located must be flooded with the liquid containing the macromolecule to be studied.

The duration of a corresponding experiment is determined by the diffusion and can thus take some time. If, for example, the concentration of the macromolecule to be studied in the liquid is only low, it can take a very long time before it has found its specific binding partner on the array. In addition, the reaction kinetics of the specific binding depends on many reaction parameters, such as for example, the temperature, the salt concentration and/or the pH which are difficult to keep constant over a fairly long time on an area of typically a few 100 $\mu m^2$ to a few $cm^2$. In order to improve the resulting limited reproducibility of the results, presently a plurality of the same molecular species are frequently provided at different locations on the microarray so that statistical predictions can thus be made.

The liquid with the macromolecule to be studied, e.g. an oligonucleotide can also be sent over a solid surface through microchannels along which macromolecules of different species are located as capture oligonucleotides ("Geniom® Technology: From DNA Chips to DNA Processors" in "Chips to Hits", 06-09 Nov. 2000, Philadelphia, Pa., USA; IBC Conferences Inc.).

The oligonucleotide to be studied thereby comes into the vicinity of all the capture oligonucleotides along the channel.

For such a prior art the microarray is, for example, a sandwich structure with external pumps on whose underside is located a CCD camera. The bottom and lid are transparent so that the fluorescence of the labelled sample oligonucleotide can be measured in the transmitted light. The liquids with the various oligonucleotides are pumped through closed channels on the array. In view of the fact that a typical channel cross-section is 100 $\mu m$ by 100 $\mu m$, a pressure of several bar is required for the necessary lengths of the channels, as a result of which both the feeds and the chip itself are expensive. The pumps and valves which carry this out, necessarily have a dead volume which leads to an increased consumption of reagents.

SUMMARY OF THE INVENTION

The object of the present invention is thus to provide a method and a device which allow an analysis having the highest possible reproducibility to be carried out with a small sample volume.

The object is solved using a method of analysis having the features herein. The object is additionally solved by a method for the manufacture of a microarray having the features herein or an analytical device having the features herein. The disclosure is also directed to advantageous developments.

In a the method, a plurality of possibly different first macromolecules is located in a known arrangement on a microarray. The microarray according to the invention is arranged on a region of a solid surface which has different wetting properties to the surrounding solid surface. A liquid having a plurality of second macromolecules which is preferably retained on this residence region, brought about by the modulation of the wetting properties, is brought onto the preferred residence region of the solid surface. After extensive removal of the liquid from the solid surface, the second macromolecules still located on the solid surface are detected in a spatially resolved fashion. From the position of these remaining second macromolecules it is determined which of the first macromolecules have formed a specific bond with macromolecules of the second plurality. The type or types of the second macromolecules contained in the liquid can be determined therefrom and/or information on their condition can be obtained therefrom.

The area on the solid which is covered by the liquid with the species of macromolecule to be analysed can be delimited by defining a preferred residence region. By selecting a corresponding geometry it is possible to keep the sample volume very small and nevertheless ensure that the second macromolecules in the liquid come in contact with all the first macromolecules arranged in the microarray. By selecting a preferred residence region by modulating the wetting properties, it is unnecessary to flood the entire chip surface with the liquid.

As a result of the different wetting properties, the liquid with the macromolecules to be studied only remains on the preferred residence region. For this purpose there is no need for any channels or ditches which would limit or retard the movement of the liquid with the macromolecules to be studied. Thus, a rapid distribution on the preferred residence region can be achieved. The surface tension of the liquid also has the effect that as a result of the different wetting properties, the liquid cannot leave the preferred residence region without the action of any external force.

The different wetting properties can be achieved, for example by means of a suitable coating either of the preferred residence region or its surroundings. For example, hydrophilic or hydrophobic regions can be defined. If the macromolecules to be studied are contained in an aqueous solution, the preferred residence region is selected, for example so that it is more hydrophilic that the surrounding solid surface. This can be achieved either by a hydrophilic coating of the preferred residence region or by hydrophobic surroundings. Hydrophobic surroundings can be achieved, for example, by a silanised surface. Depending on the wetting properties of the liquid in which the macromolecules to be studied are contained, the solid surface surrounding the residence region can also be selected to be hydrophilic, lipophobic or lipohilic compared to the surface of the preferred residence region.

The wetting properties can furthermore be modulated by microstructuring, as is the case with the so-called lotus effect which is based on the different roughness of the surface. In this case, the different roughness brings about different wetting properties. The roughness can be obtained, for example, by microstructuring the corresponding surface regions, e.g., by chemical treatment or ion irradiation.

The production of regions of different wetting properties is simple and cheap using already known lithographic methods and/or coating technologies.

Since the device according to the invention requires no mechanical limitations such as channels for example, it is also possible to load only partial regions of the microarray with liquid. Such an application is advantageous if merely a special analysis is required which need not include all the macromolecules present on the array.

This object is solved by a method according to the invention according to claim 2. In this development a microarray is used on which a plurality of at least partly different first macromolecules is located in a known arrangement. The liquid with the plurality of second macromolecules is brought into the region of the microarray on the solid surface. At least one surface wave is launched in the direction of the liquid. Distribution and/or thorough mixing of the liquid can be achieved by pulse transmission to the liquid so that the second macromolecules can come in contact with the first macromolecules effectively and quickly. As in the first development the liquid is then largely removed from the region of the array and the positions on the microarray at which second macromolecules have formed a bond with the first macromolecules and are thus still present on the solid surface are determined in a spatially resolved fashion.

In this development of the method the macromolecules contained in the liquid are thoroughly mixed with the aid of the surface wave and effectively distributed on the solid surface. In this way the liquid is quasi-stirred. Long reaction times, such as are required in conventional methods, can thus be reduced since the motion of the molecules is not accomplished by diffusion. In addition, in the method according to the invention according to the second development, other transport or mixing devices such as micromechanical or piezoelectrically driven pumps can be dispensed with.

The distribution of the liquid and the thorough mixing takes place almost without pressure. The mixing of the liquid by the surface wave produces homogeneous reaction conditions, e.g. with respect to temperature, pH or salt concentration in the entire region covered by the surface wave.

The surface wave can be generated using at least one surface wave generating device. The surface waves transmit a pulse to the liquid with the macromolecules to be studied. The pulse transmission is achieved either by the mechanical deformation of the solid surface or by the force effect of the accompanying electric fields on charged or polarisable material.

In this case, the strength of the force effect on the liquid can be adjusted over a wide range via the amplitude of the surface wave. The surface wave can be generated in a pulsed fashion with pulses of different length or continuously. It is possible to control the surface wave generating device using appropriate software.

Surface waves can be generated on piezoelectric substrates or substrates with piezoelectric regions, e.g. piezoelectric coatings. In this case, it is sufficient if the substrate or the corresponding coating is only present in the region in which the surface wave generating device is located. The surface acoustic wave then also propagates outside the piezoelectric region.

An inherently known interdigital transducer is advantageously used to generate the surface wave. In the simplest design such an interdigital transducer has two electrodes which intermesh in a finger-like fashion. By applying a high-frequency alternating field, e.g. of the order of magnitude of a few 100 MHz, a surface wave is excited in a piezoelectric substrate or in a piezoelectric region of the substrate, whose wavelength is obtained as the quotient of the surface acoustic velocity and the frequency. The direction of propagation is perpendicular to the intermeshing finger electrode structure. Using such an interdigital transducer a very defined surface wave can thus be generated in a simple fashion. The interdigital transducer is manufactured cheaply and simply using known lithographic methods and coating technologies. Interdigital transducers can also be controlled without wires, e.g. by emitting an electromagnetic alternating field in an antenna device connected to the interdigital transducer.

In an advantageous development a laterally bounded sound path of the surface wave can be achieved if the finger spacing of the interdigital transducer between the electrodes is varied. At a given frequency, the resonance condition that the frequency is equal to the quotient of the surface acoustic velocity and the finger spacing is only satisfied in a laterally spatially bounded region. Thus, with such a so-called tapered transducer a selected region can be specifically acoustically irradiated with a surface wave.

A combination of the methods is especially advantageous.

Advantageous developments of the method according to the invention are the subject matter herein.

The geometry of the preferred residence region can be matched to the corresponding application. For example, the preferred residence region can be guided in a meander-shaped fashion through the microarray so that the individual positions of the microarray are lined up along the preferred residence region. In this case, it is ensured that all the points of analysis come in contact with the liquid. A cross-wise arrangement can also be provided wherein the individual positions of the microarray are located in the crossing regions. In a simple development the micro-array is arranged on a bounded residence region which closely surrounds the individual analysis points of the microarray.

The spatially resolved measurement of the second macromolecules remaining on the solid surface after removal of the liquid, which have thus hybridised with the first macromolecules can be carried out using a fluorescence measurement. For this purpose the macromolecules to be analysed must be labelled with a fluorescent dye or have a fluorescent component.

Alternatively, the macromolecules to be analysed can be provided with an electrically active function group or comprise one such group. The spatially resolved measurement can then be implemented as an electrical measurement.

The conductivity or dielectric properties of the second macromolecules can also be used for detection.

The second macromolecules can also be radioactively marked so that the position of the remaining second macromolecules can be determined after the liquid has largely been removed.

Another possibility is obtained by using so-called "beads". Such, e.g. 10 µm-sized mass particles are functionalised such that they only adhere to certain macromolecules. The positions on the microarray at which such beads, are located can then be determined subsequently. Thus, information can be obtained on the condition and species of the macromolecules in the microarray itself. The beads can be determined, for example, as a mass coating at the individual point on the microarray. In this case, the fact that a surface acoustic wave is damped by a mass coating on the surface can be utilised, for example. If a laterally bounded surface acoustic wave is launched over the solid surface using a tapered interdigital transducer as described above so that it only encounters one or a few points on the microarray, it can be determined via the damping of this surface wave whether or not an additional mass in the form of beads is located at these points.

The method according to the invention can advantageously be used, for example, for the analysis of oligonucleotides. Various oligonucleotides are located in a known arrangement on the array. The liquid with the oligonucleotide to be analysed is brought onto the microarray. The location at which oligonucleotides in the liquid have specifically bound or hybridised with oligonucleotides in the microarray is established in a spatially resolved fashion. The method is especially suitable for DNA screening wherein the oligonucleotides consist, for example, of short DNA strands (deoxyribonucleic acid strands). However, various proteins, various antigens or various antibodies can also be provided or analysed in the microarray.

In an advantageous further development of the method according to the invention at least one surface wave is launched over the solid surface after applying the liquid to the solid surface. The binding strength can be determined from the intensity of the surface wave required to release the binding of the macromolecules in the microarray with the macromolecules in the liquid. In this case, both the mechanical deformation of the solid surface and the force of the electric field accompanying the deformation can release the binding.

Using two surface waves whose sound paths have limited width and are incident on the microarray from different directions, a single point can be selected to check the binding strength on the microarray. The deformation of the solid is largest at the point of intersection of the surface waves. A macromolecule binding located there will be exposed to a greater loading than the bindings in the vicinity where the surface waves do not intersect.

For example, in a fluorescence measurement of the second macromolecules the surface wave amplitude will be increased and the fluorescence signal measured in a spatially resolved fashion. If the binding between the first and second macromolecules is broken by the increased amplitude at the location of the fluorescence, the fluorescence signal thereby changes.

Surface waves can be used, for example, to transport the quantity of liquid into the region of the microarray or to remove the liquid from the microarray. For example, a surface wave can be used to drive the liquid in the direction of the microarray from a reservoir located on the solid surface and formed, for example, by a region whose wetting properties are selected such that the liquid preferably remains thereon. After the experiment has been completed, the region of the microarray can be acoustically irradiated with a surface wave such that the liquid driven by the pulse transmission of the surface wave leaves the microarray again. At a very high surface wave intensity it is also possible to completely remove the liquid from the entire solid surface.

If the intensity is suitably selected, the acoustic irradiation of the solid surface with the surface acoustic wave also brings about cleaning of the covered areas.

The use of surface waves for thorough mixing or distribution of the liquid on the solid surface avoids dead volumes which arise with conventional pump arrangements. There are no long leads and valves which must be "pumped free". Surface waves can also be used to generate turbulence over large distances with the smallest quantities of fluid. In this way, the average velocity of the macromolecules to be studied is increased and the reaction time thus reduced. Surface waves can thus advantageously be used to apply and mix sample substances in order to accelerate the reaction time in an otherwise diffusion-dependent process.

Using a liquid with known second macromolecules, the species of the possibly unknown first macromolecules on the microarray can be determined or characterised in a similar fashion.

In a method according to the invention for the manufacture of a microarray, a liquid with at least one species of macromolecule is applied to a region of a solid surface whose wetting properties differ from the surrounding solid surface such that the liquid preferably stays thereon. The macromolecules are terminated with a light-active inhibitor which prevents any binding with the surface. Again as a result of the surface tension and the wetting properties, the liquid cannot leave the preferred region of the surface without the action of an external force. The liquid is thus already localised without the need to flood the entire solid surface with the liquid. In this way, the necessary quantity of reagent is reduced.

A subregion of the preferred residence region is locally illuminated in order to release the inhibitor of the macromolecules in the illuminated region. The macromolecules in the illuminated subregion can now be bound and are bound at the illuminated locations in the preferred residence region. In this way the position of the residence region at which the macromolecule should be located can be determined precisely.

If necessary, these steps are repeated with one or a plurality of different species of macromolecules in order to immobilise various macromolecules at defined and known positions of the preferred residence region. By specifying a preferred residence region by selecting its known properties, channels, edges, ditches and other mechanical hindrances are avoided. The liquid can move freely in the preferred residence region before binding.

Surface waves can advantageously also be used for liquid transport and thorough mixing during the construction of the microarray from the first macromolecules for photoinduced synthesis, e.g., for the synthesis of DNA. The liquid transport is no longer diffusion-dependent and a homogeneous liquid distribution is ensured. Other advantages are obtained in a similar fashion as in the method of analysis described above.

BRIEF DESCRIPTION OF THE DRAWINGS

Developments of the method according to the invention are explained in detail with reference to the drawings which are not to scale. In the figures.

DESCRIPTION OF THE PREFERRED EMBODIMENTS

The representation of the figures should be understood as showing possibly only one part of a larger system in which further analytical or synthesis devices of the type according to the invention or another type are located.

Figure 1:
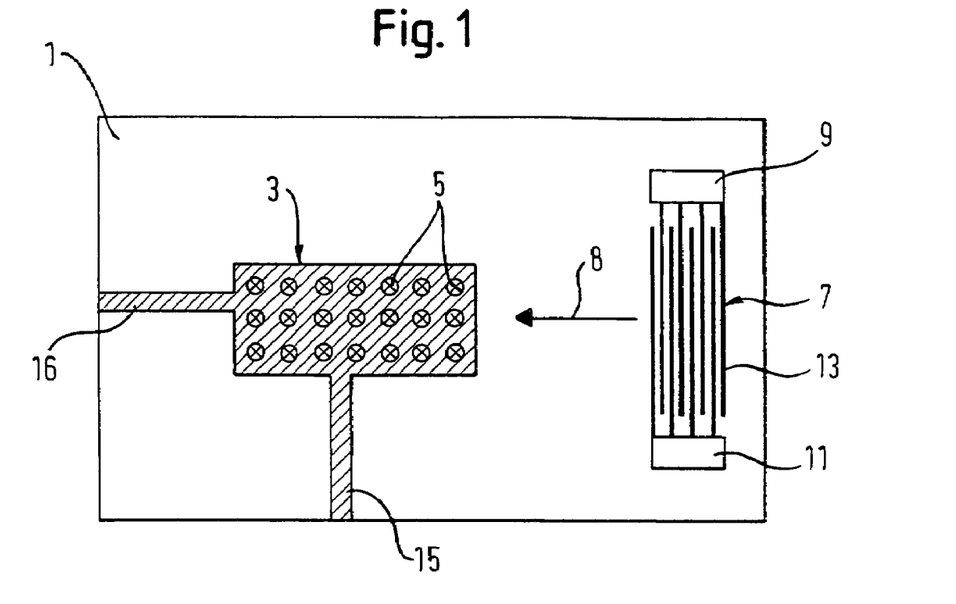
FIG. 1: is a schematic diagram of a device for implementing a method according to the invention.

In FIG. 1, 1 denotes a solid, e.g., made of piezoelectric material such as quartz or LiNbO$_3$. Alternatively a solid can be provided which has at least a partly piezoelectric surface, e.g. made of ZnO. In this case, 1 can be a section of a larger chip unit.

Located on the solid surface is a preferred residence region 3 which has wetting properties different to the surrounding solid surface. The surface of the region 3 is selected such that the liquid in which the material to be studied is located, preferably stays thereon. For an aqueous solution the surface in the preferred residence region 3 is for example, selected to be hydrophilic compared with the more hydrophobic surface of the surrounding solid. For this purpose, for example, the remaining solid surface can be silanised or microstructured and thereby hydrophobic.

5 denotes, for example, a position for a species of macromolecules which are located in the residence region 3. However, very many more positions 5 can also be provided. 15 denotes a feed on the solid 1 which has the same surface properties as the preferred residence region 3, 16 denotes a corresponding drain. Feed and drain can naturally also be exchanged. In a fashion not shown in further detail here 15 and 16 lead, for example, to a reservoir or other analysis stations.

Figure 5A:
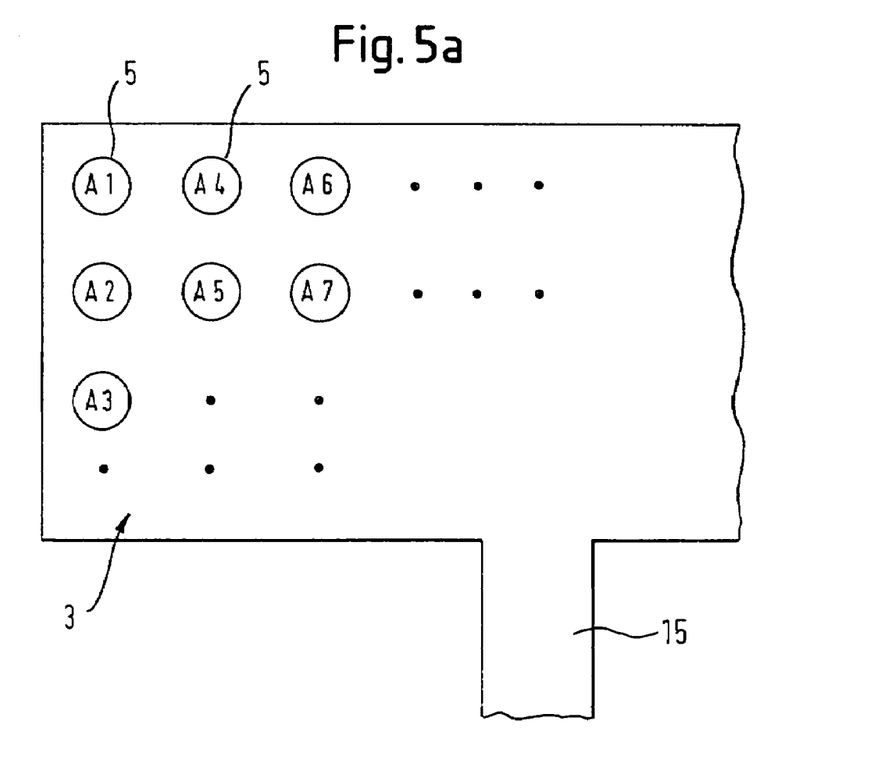

FIG. 5a shows an enlarged part of region 3. Only a few of the positions 5 are indicated.

7 denotes an interdigital transducer which is used as a surface wave generating device. The interdigital transducer 7 consists of two electrodes 9 and 11 with finger-like extensions 13 which mesh into one another. When an alternating field is applied to the electrodes of the transducer, a surface wave is generated having a wavelength corresponding to the finger spacing of the electrodes. The direction of propagation is perpendicular to the intermeshing fingers in the direction 8. The transducer comprises a large number of intermeshing fingers of which only a few are shown schematically and not to scale.

By selecting the crystal orientation and/or the geometry of the interdigital transducer, various types of waves can be produced, such as for example Rayleigh waves or shear waves. The interdigital transducer 7 is produced for example using lithographic methods and coating methods on the chip surface.

Naturally, a plurality of transducers possibly with different directions of irradiation can be arranged around the microarray in a fashion not shown.

Such a device according to the invention can be used as follows. Oligonucleotides are described below as an example for the macromolecules.

In the microarray according to the invention various types of DNA strands "A1", "A2", "A3 . . . ", so-called oligonucleotides are brought onto the individual positions 5 of the microarrays (see, for example, FIG. 5a). The type of strand, determined by the sequence of the bases adenine, cytosine, guanine and thymine, is known and is given by the position in the matrix. Typical distances between different types of oligonucleotides are approximately 100 µm and the strands are typically 10 to 100 base pairs long. The oligonucleotide sample to be identified (in the following for example "a1") is labelled with a fluorescence dye or an electrically active function group and is brought, dissolved in a liquid, onto the array via the feed 15. The wetting properties of the feed 15 are selected so that the liquid does not leave this region 15 laterally.

The liquid is distributed on the preferred residence region 3. After the liquid is located on the region 3, a surface wave is generated in the direction 8 using an interdigital transducer 7. For this purpose an alternating field of a few megahertz is applied to the electrodes 9, 11, for example, using contact wires. Alternatively, an alternating field can be emitted into an antenna device connected to the electrodes. The surface wave propagates in the direction 8 and by pulse transmission to the liquid, promotes its thorough mixing and distribution on the preferred residence surface 3. In this way it is ensured that the liquid moves over the entire area 3 and comes in connection with all the analysis points 5 of the microarray.

A surface wave generated by an interdigital transducer not visible on the section in FIG. 1 can also be used for the movement along the feed 15. In each case, the amplitudes of the surface waves are selected so that the liquid does not leave the preferred region 3, 15, 16.

If a "capture oligonucleotide A1" complementary to the sample is present at one of the positions 5 in the array, hybridisation takes place between the complementary oligonucleotides "a1" and "A1".

The sample solution is then washed from the array through the outlet 16 by the action of a surface wave in the direction 8. The electrically active or fluorescent marker is only still present at those places where the sample oligonucleotide "a1" has hybridised with a capture oligonucleotide. The fluorescence or the electrical signal is now measured in a spatially resolved fashion. From the position of the signal it is determined with which of the. DNA strands located on the. microarray the sample oligonucleotide "a1" has hybridised. The sample oligonucleotide "a1" can thus be identified.

The sample oligonucleotide is effectively brought onto the capture oligonucleotide at the points 5 on the microarray as a result of the bounded residence region 3. As a result of the additional mixing and distribution, the reaction times are significantly reduced.

The various types of DNA strands "A1", "A2", "A3" . . . can be applied to the matrix form of the microarray using a pipetting robot for example.

In an especially advantageous method these so-called capture oligonucleotides are produced on the microarray itself by photo-induced synthesising. The individual bases for the oligonucleotide synthesising are each terminated with a light-active inhibitor. The oligonucleotide can only be lengthened at those points on which the light is incident. A dissolved base, e.g. guanine is applied to the preferred residence region 3. A light beam locally releases the inhibitors at a location 5 at which the guanine should dock. After a certain waiting time the reaction has taken place at the pre-designated points. This reaction can also be accelerated by mixing with a surface wave using an interdigital transducer 7. After the reaction, the liquid with the guanine is again removed from the array. Now the same step can be repeated with another base, e.g. cytosine. In this way a microarray is produced with different DNA strands being located at individual locations.

Figure 2:
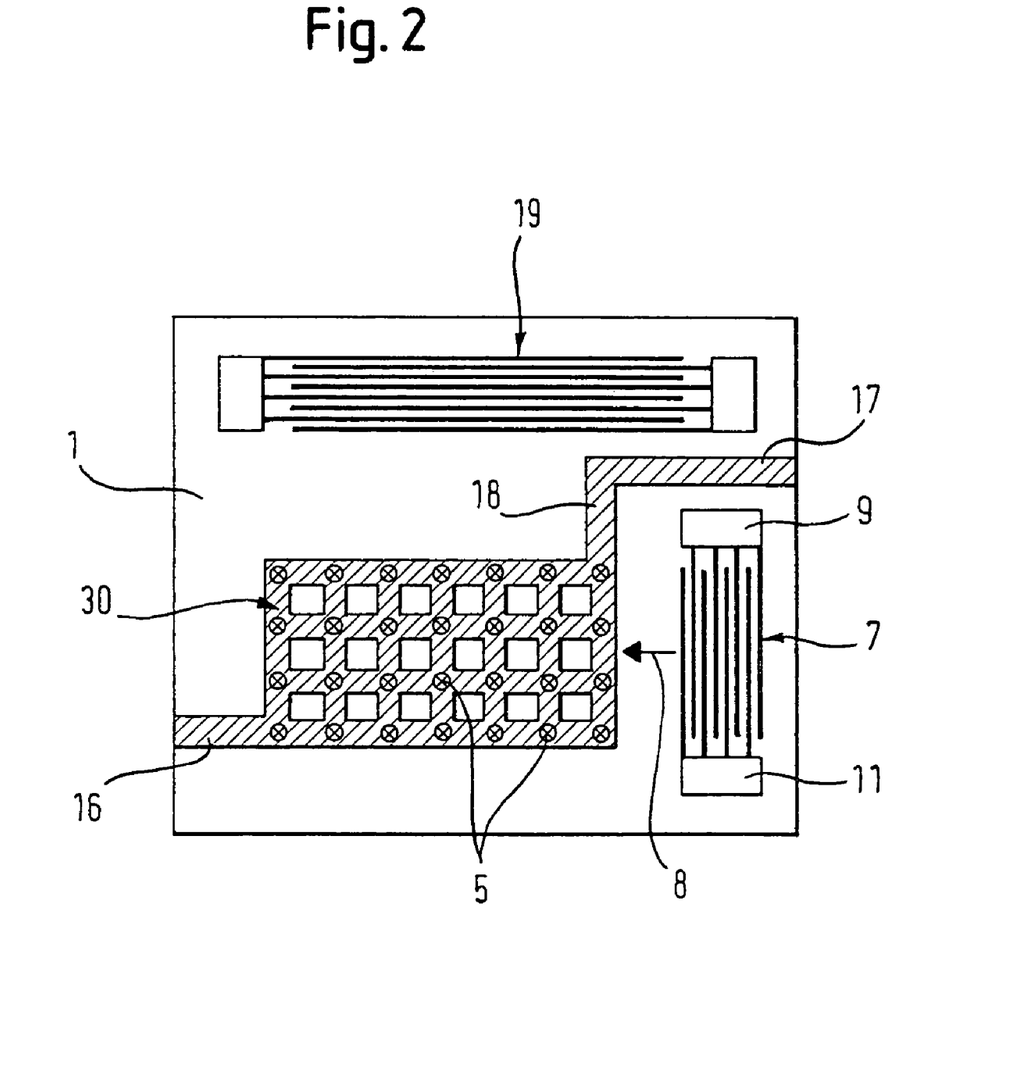
FIG. 2: is a schematic diagram of a further device for implementing a method according to the invention.

FIG. 2 shows a different embodiment with which the method according to the invention can be implemented. A section from a chip surface is again shown. In this case the preferred residence region 30 is arranged in a cross-shaped fashion and again shown hatched. The analysis points 5 are located at the points of intersection. A second interdigital transducer 19 having a direction of emission perpendicular to the direction of emission 8 of the first interdigital transducer 7 is provided on one side of the microarray.

By using such a second interdigital transducer 19 the mixing or distribution of the liquid with the sample oligonucleotide "a1" can be promoted even more strongly. Naturally corresponding interdigital transducers can also be provided on the remaining sides of the microarray.

The liquid can be brought onto the feed 17. As soon as this has reached the region 18, it can be driven with the aid of an interdigital transducer 19 having a direction of emission directed along the feed 18. Any following liquid can be entrained on the region 17 as a result of the surface tension.

The quantity of liquid thus reaches the preferred residence region 30. There the liquid can be effectively distributed and thoroughly mixed with the aid of the interdigital transducer 7 and 19. The interdigital transducer 7 provides a movement component in the horizontal direction of FIG. 2 while the interdigital transducer component 19 provides a movement component in the perpendicular direction in FIG. 2. Thus, an optimal distribution of the liquid with a sample nucleotide on the microarray in FIG. 2 can be achieved in a simple and rapid fashion.

After the experiment has been completed, the quantity of liquid is guided via the outlet 16 by means of a surface wave generated using the interdigital transducer 7, via the outlet 16 into a reservoir not shown, which can also be located in the chip surface. The feeds or outlets 16, 17 and 18 in FIG. 2 are functionalised like the preferred residence region 30.

In the embodiment shown in FIG. 2 the first macromolecules can also be applied as in the embodiment in FIG. 1. The crosswise arrangement of the residence region 30 in the embodiment in FIG. 2 reduces the quantity of liquid required to bring the sample nucleotide effectively into the region of all the capture nucleotides "A1", "A2", "A3"...

Figure 3:
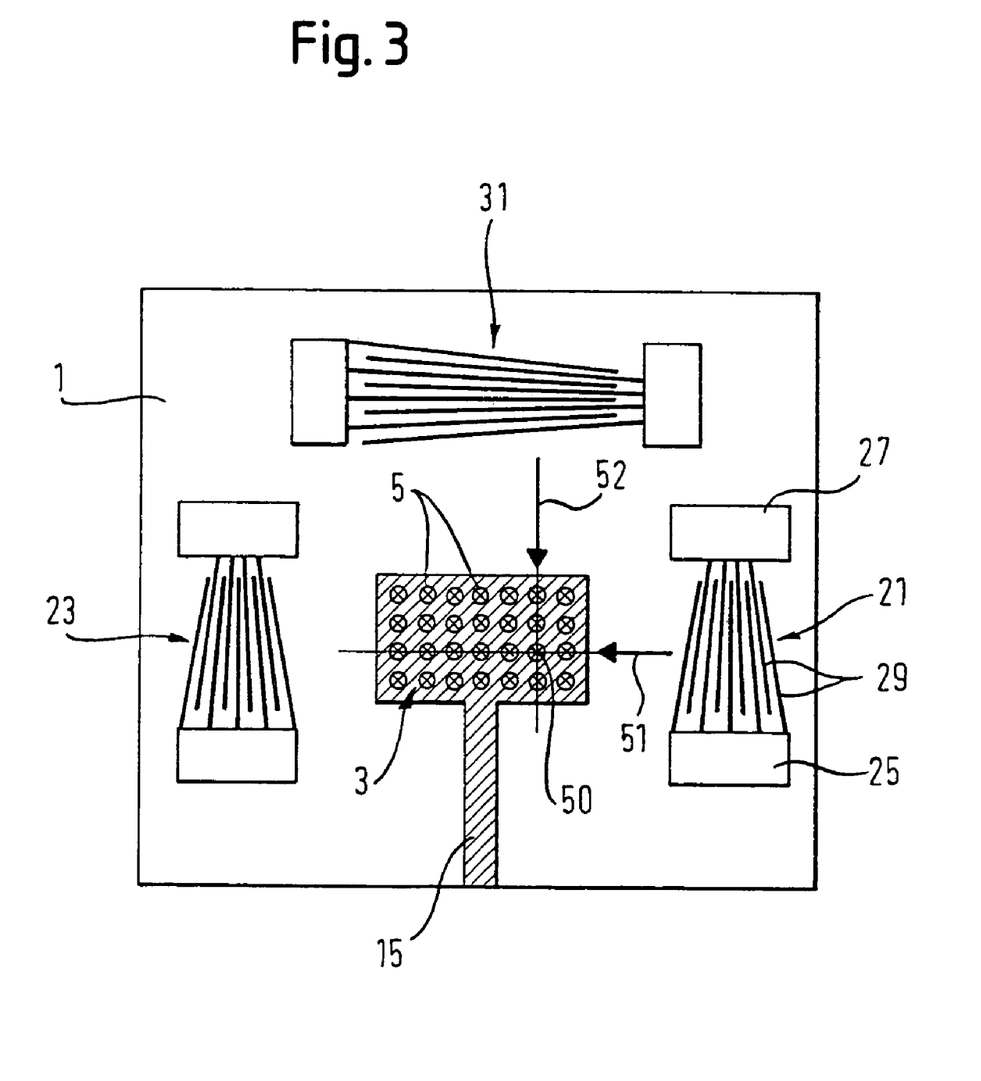
FIG. 3: is a schematic diagram of a third device for implementing a method according to the invention.

FIG. 3 shows a different embodiment again as a section of a chip surface. In this case the interdigital transducers 21, 23 and 31 are configured as so-called "tapered" interdigital transducers. The interdigital transducer 21 comprises electrodes 25 and 27 with finger-like extensions 29. The spacing of these fingers is not constant along the connecting axis between the electrodes 25 and 27. The finger spacing determines the wavelength of the emitted surface wave. At constant surface wave acoustic velocity, the resonance condition that the frequency of the surface wave is obtained as a quotient of the surface acoustic velocity and the wavelength is only satisfied at a certain applied frequency i.e. for a certain finger spacing. In this way, a surface wave can be generated which has only a very small lateral expansion perpendicular to the direction of propagation and a defined position along the axis of the transducer.

The interdigital transducers 23 and 31 are constructed similarly with the direction of propagation of the surface wave of the interdigital transducer 23 being opposite to the direction of propagation of the surface wave of the interdigital transducer 21. The interdigital transducer 31 has a direction of propagation perpendicular thereto. In this case, additional interdigital transducers can naturally also be provided, e.g. an interdigital transducer having a direction of propagation opposite to a direction of propagation of the interdigital transducer 31.

A surface wave generated using the interdigital transducer 21 having the direction of propagation 51 is shown as an example. 52 denotes the direction of propagation of a surface wave which can be generated with the interdigital transducer 31. By selecting the frequency of the surface wave at the two interdigital transducers, it is possible to select the analysis point 50 at which the maximum intensity occurs.

Such a device can advantageously be used as follows.

Figure 5B:
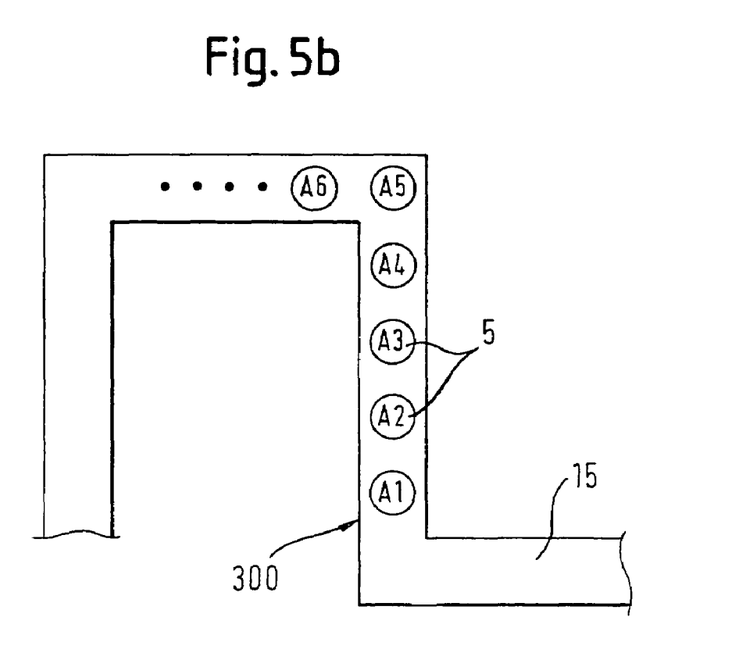

First, a liquid, for example, with the sample oligonucleotide "a1" is applied via the feed 15 to the preferred residence region 3 on which various capture nucleotides "A1", "A2", "A3"... are located, as shown in FIG. 5*b*. The mixing and distribution of the liquid with the sample oligonucleotide "a1" on the preferred region 3 is accelerated by irradiation of a surface wave. After the reaction time the liquid is again washed largely away from the surface and the sample oligonucleotide "a1" only remains at the locations at which the sample oligonucleotide "a1" hybridises with a capture oligonucleotide "A1" on the microarray. The surface wave is then displaced along the connecting line between the electrodes 25 and 27 by using various frequencies.

A spatially resolved measurement is used to determine at which of the macromolecules the sample nucleotide "a1" has hybridised. For this purpose, a fluorescence measurement can again be carried out, as already described above.

Using the tapered interdigital transducer 21, a surface wave can now be produced which precisely targets the analysis point. So at which the oligonucleotide "a1" is located after hybridisation. By emitting a surface wave having the opposite direction of propagation but the same frequency, a dynamic potential can be produced at the location of the sample oligonucleotide "a1" using the interdigital transducer 23. The higher the intensity of the surface waves, the stronger is the pulse transmission. From a certain intensity of the dynamic potential the binding between "a1" and the corresponding capture nucleotide "A1" is broken and the fluorescing oligonucleotide "a1" leaves the location in the microarray. In this way the binding strength of the sample oligonucleotide "a1" at the corresponding position on the microarray can be checked. The force transmission to the bond can be produced using the surface waves both mechanically and also electrically by the electric fields accompanying the deformation of the solid surface. In order to select a specific analysis point 50, two interdigital transducers 21 or 31 having directions of propagation 51 or 52 perpendicular to one another can be used as described above.

From the binding strength thus characterised, it can be determined, for example, whether the sample oligonucleotide and the capture oligonucleotide 19 have complementary base pairs or 20.

After the experiment has been completed, the interdigital transducer 31 can be used to generate a surface wave with which the liquid can be driven away from the region of analysis 3 via the feed or outlet channel 15.

Figure 4:
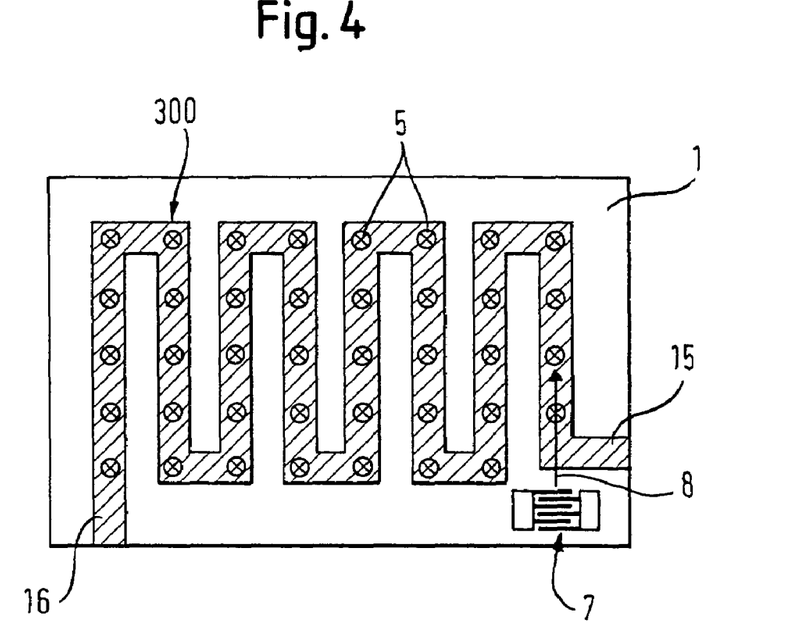
FIG. 4: is a schematic diagram of a fourth device for implementing a method according to the invention and FIG. 5a and/or b: show enlarged sections of the devices shown in FIG. 1 or 4, respectively.

In an embodiment in FIG. 4 the residence region 300 is configured as meander-shaped with the capture oligonucleotides being lined up along this meander-shaped region. FIG. 5*b* shows a section of the region 300. Again only a few of the positions 5 are shown as an example. Using the interdigital transducer 7 the quantity of liquid can be driven along this meander-shaped residence region so as to ensure that the sample nucleotide in the liquid comes in the immediate vicinity of the capture oligonucleotides. In order to support the movement along the meander-shaped residence region 300, other interdigital transducers not shown can be provided.

Naturally, the various geometries as shown for example in FIGS. 1 and 4 can also be combined. Finally, in each of the embodiments additional interdigital transducers can be used to intensify the effects according to the invention.

Each of the individual devices can be part of a larger complex on a solid surface on which a plurality of analysis stations and/or reservoirs for liquids are located in order to achieve a network or a so-called "lab on the chip".

The invention claimed is:

1. A method for analyzing macromolecules comprising the steps of:
   locating a plurality of first at least partly different macromolecules in a known arrangement on a microarray comprising a specific region wherein the specific region has different wetting properties from its surrounding regions on the microarray such that a liquid comprising a plurality of second macromolecules can reside on the specific region,
   arranging the microarray on a solid surface and loading the liquid comprising the plurality of the second macromolecules onto a region of the microarray,
   launching a surface wave and distributing the liquid on the microarray with the aid of the surface wave such that the plurality of the second macromolecules are moved to the specific region and interact with the first at least partly different macromolecules,
   after a period of time, removing the liquid from the specific region on the microarray, and
   analyzing the second macromolecules remaining on the specific region after the removal step and determining the positions of the first at least partly different macromolecules on the specific region of the microarray wherein the first at least partly different macromolecules form bonds with the second macromolecules remaining on the specific region after the removal step and wherein the first at least partly different macromolecules comprises different oligonucleotides and/or different proteins and/or different antigens and/or different antibodies.

2. The method according to claim 1 wherein the second macromolecules are labelled with a fluorescent dye or have a fluorescent component and the step of analyzing the second macromolecules remaining on the specific region after the removal step comprises fluorescence measurement.

3. The method according to claim 1 wherein the second macromolecules are radioactively labelled.

4. The method according to claim 1 wherein the liquid is removed from the microarray by launching a surface wave.

5. The method according to claim 1 wherein the liquid is removed from the microarray by launching a surface wave and acoustically irradiating the solid surface by the surface wave.

6. The method according to claim 1 wherein the first at least partly different macromolecules are oligonucleotides.

7. The method according to claim 1, wherein the second macromolecules are oligonucleotides.

8. The method according to claim 1 or 6 or 7, wherein the oligonucleotides are deoxyribonucleic acids.

* * * * *